US007409952B2

(12) United States Patent
Chen

(10) Patent No.: US 7,409,952 B2
(45) Date of Patent: Aug. 12, 2008

(54) PORTABLE BREATHING APPARATUS

(76) Inventor: Yu-Hu Chen, 3F, No. 2, Lane 55, May-Kwei Rd., Hsintien City, Taipei Hsien (TW)

( * ) Notice: Subject to any disclaimer, the term of this patent is extended or adjusted under 35 U.S.C. 154(b) by 561 days.

(21) Appl. No.: 11/017,979

(22) Filed: Dec. 20, 2004

(65) Prior Publication Data

US 2006/0130834 A1 Jun. 22, 2006

(51) Int. Cl.
*A61L 9/20* (2006.01)

(52) U.S. Cl. ............................ 128/204.18; 128/205.24; 250/455.11; 422/120

(58) Field of Classification Search ............ 128/204.21, 128/204.18, 205.24, 205.23, 204.23, 205.25; 422/120, 121, 122; 250/455.11; 96/224
See application file for complete search history.

(56) References Cited

U.S. PATENT DOCUMENTS

| | | | | |
|---|---|---|---|---|
| 5,398,676 | A * | 3/1995 | Press et al. | 128/204.23 |
| 5,427,090 | A * | 6/1995 | Hipskind et al. | 128/205.12 |
| 5,993,738 | A * | 11/1999 | Goswani | 422/22 |
| 6,119,689 | A * | 9/2000 | Korman | 128/205.29 |
| 6,716,406 | B2 * | 4/2004 | Reisfeld et al. | 423/245.1 |
| 2003/0086831 | A1 * | 5/2003 | Horton, III | 422/120 |
| 2005/0186108 | A1 * | 8/2005 | Fields | 422/4 |
| 2007/0022879 | A1 * | 2/2007 | Aiba | 95/58 |

* cited by examiner

*Primary Examiner*—Steven O Douglas
(74) *Attorney, Agent, or Firm*—patenttm.us

(57) ABSTRACT

A portable breathing apparatus has a respirator and a filter. The filter has a multifunctional strainer, a photocatalyst element, an exhauster, a high-pressure generator and an active carbon net in the interior thereof. Via the exhauster, external air can be filtered by the multifunctional strainer and mixed with ozone and negative ions generated from the photocatalyst element and the high-pressure generator thereby filtering and sterilizing the external air. Furthermore, the external air passes through a tube via the active carbon net to the respirator. Hence, it is easy for people wearing the portable breathing apparatus to breathe and experience the functions of air sterilization and filtration.

6 Claims, 4 Drawing Sheets

PORTABLE BREATHING APPARATUS

BACKGROUND OF THE INVENTION

1. Field of the Invention

The present invention relates to a portable breathing apparatus, and more particularly to a portable breathing apparatus with which it is easy for people to breathe and experience the functions of air sterilization and filtration.

2. Description of Related Art

In times of epidemics, such as SARS, people wear all kinds of respirators, such as surgery respirators, N95 respirators and P100 respirators, to prevent being infected by viruses. However, when wearing a conventional respirator with multilayer materials to prevent infectious droplets or viruses, it is difficult for a user to breathe. Furthermore, the conventional respirator only has an effect to filter the viruses and does not sterilize the viruses so that the user still has an opportunity to inhale the virus thereby catching a disease.

Therefore, the invention provides a portable breathing apparatus to mitigate or obviate the aforementioned problems.

SUMMARY OF THE INVENTION

The main objective of the present invention is to provide a portable breathing apparatus with which it is easy for people to breathe and experience the functions of air sterilization and filtration.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
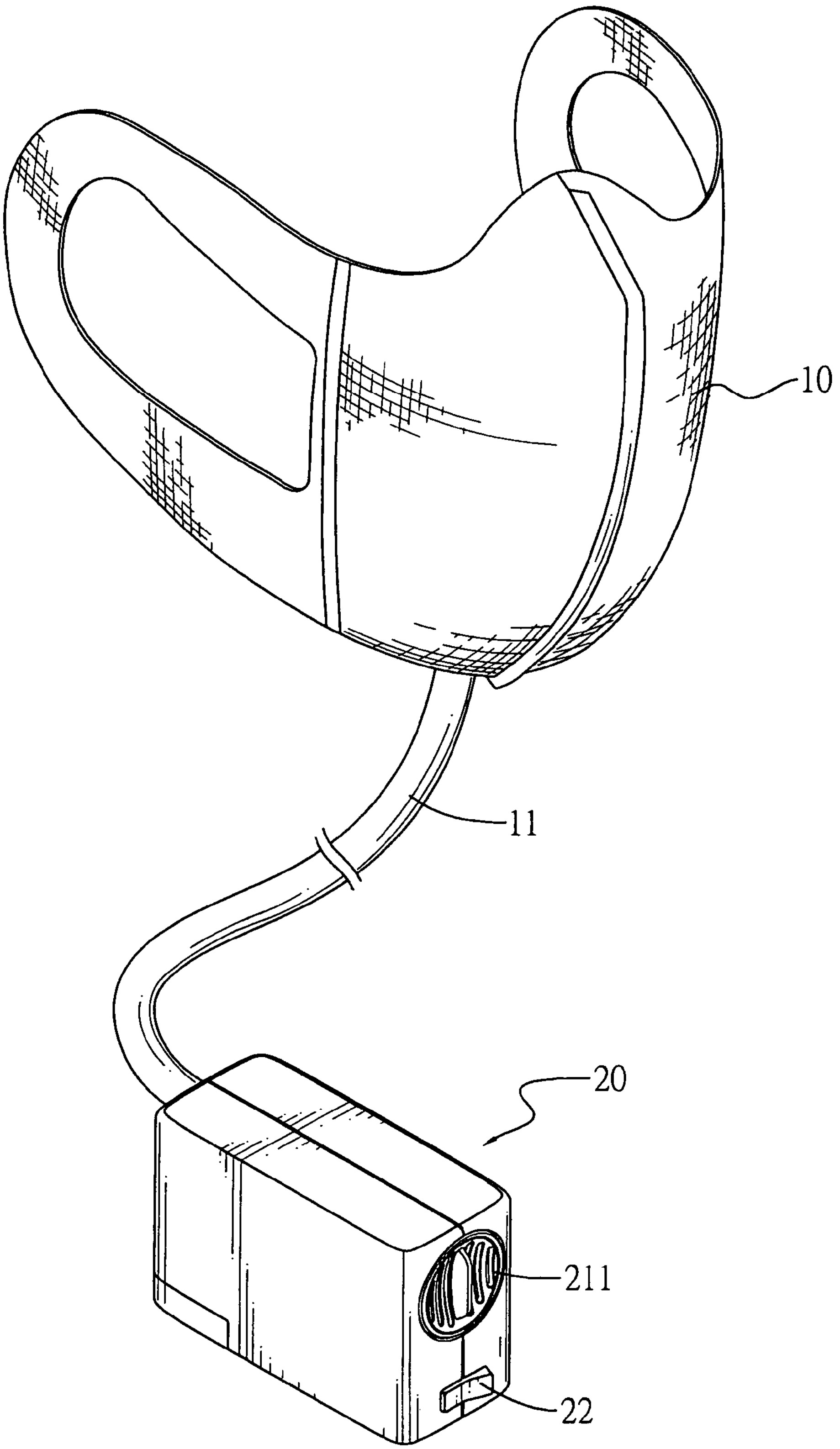
FIG. 1 is a perspective view of a portable breathing apparatus in accordance with the present invention.
Figure 2:
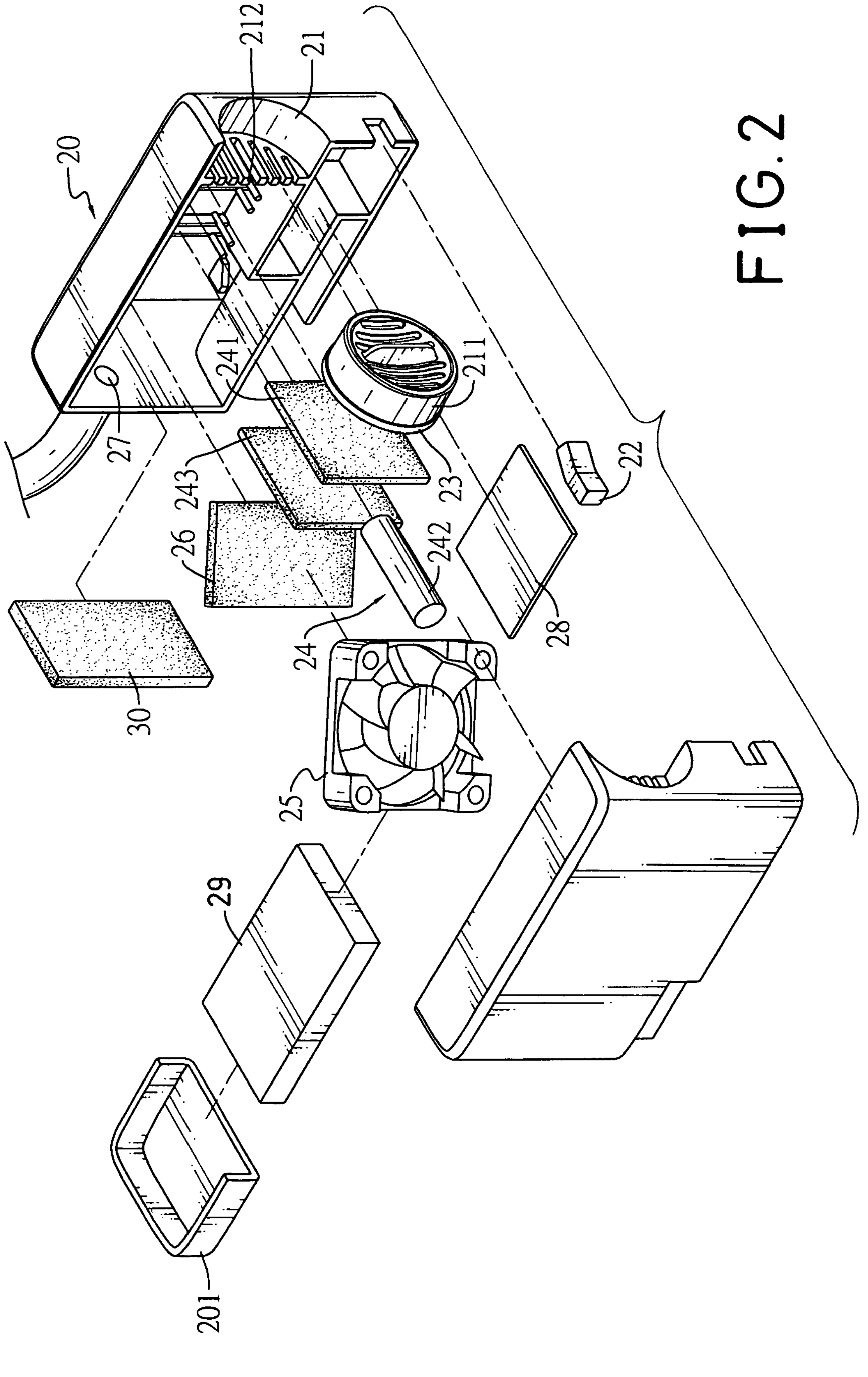
FIG. 2 is a first exploded perspective view of the portable breathing apparatus in accordance with the present invention.
Figure 3:
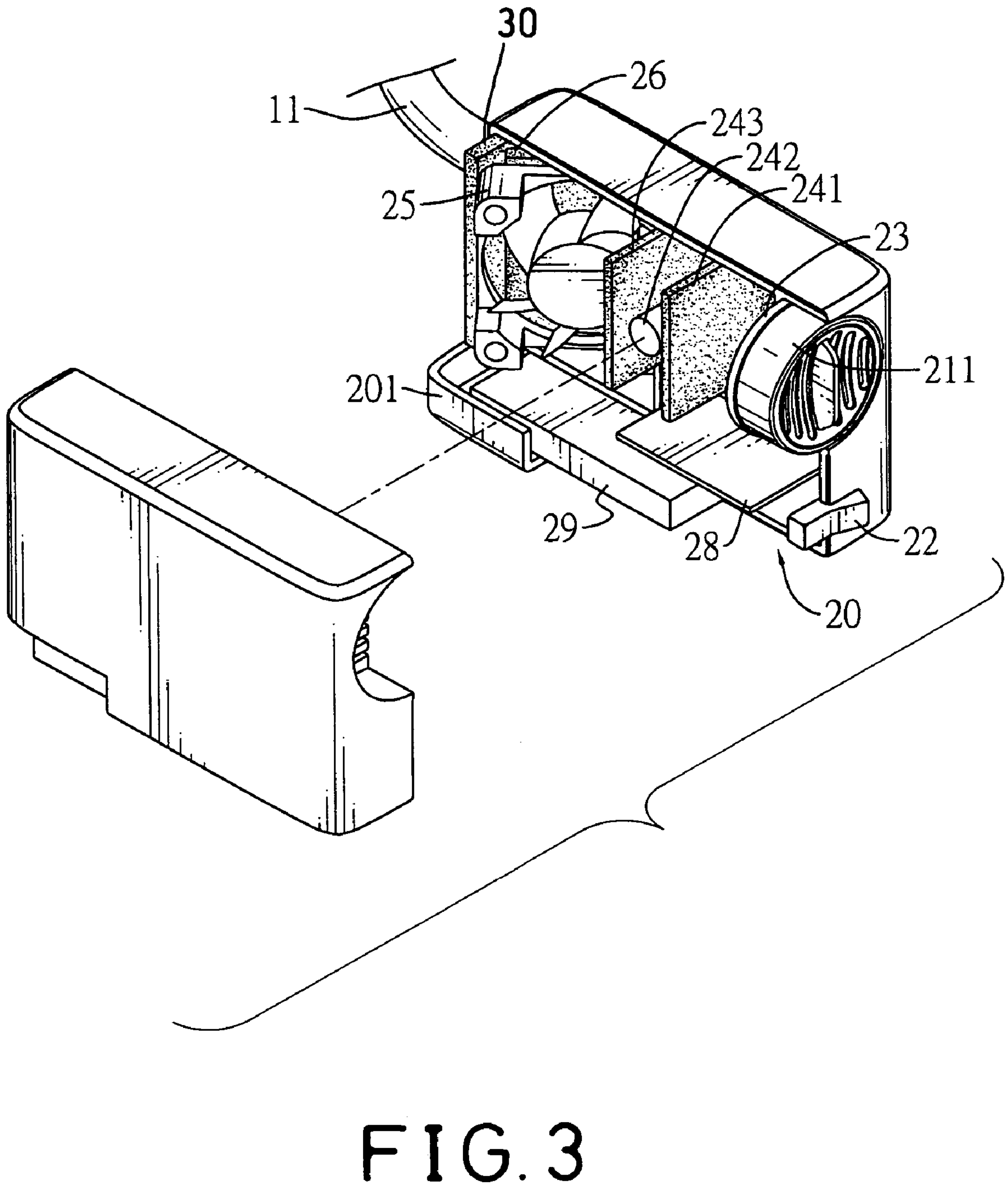
FIG. 3 is a second exploded perspective view of the portable breathing apparatus in accordance with the present invention.

With reference to FIGS. 1-3, a portable breathing apparatus comprises a respirator (10) and a filter (20).

The filter (20) has a hollow shell and a chamber defined in the hollow shell. A hole (21), which is an entry for external air, is defined in a front end of the hollow shell. A switch (22) is provided under the hole (21) to switch on or off the filter (20). A vane cap (211), in which multiple fans can be received, is inserted into the hole (21) and multiple rods (212) are provided in the chamber and adjacent the vane cap (211). An opening (27), from which the external air is expelled from the chamber, is defined in a rear end of the shell. A tube (11), which is inserted into the opening (27), is connected to the filter (20) and the respirator (10).

A multifunctional strainer (23), a photocatalyst element (24), an exhauster (25), a high-pressure generator (26) and an active carbon net (30) are provided in the chamber in turn. The exhauster (25) can be a fan or a compressor and the multifunctional strainer (23) is provided between the vane cap (211) and the rods (212). The exhauster (25), the high-pressure generator (26) and the active carbon net (30) are provided adjacent the opening (27) in turn.

Figure 4:
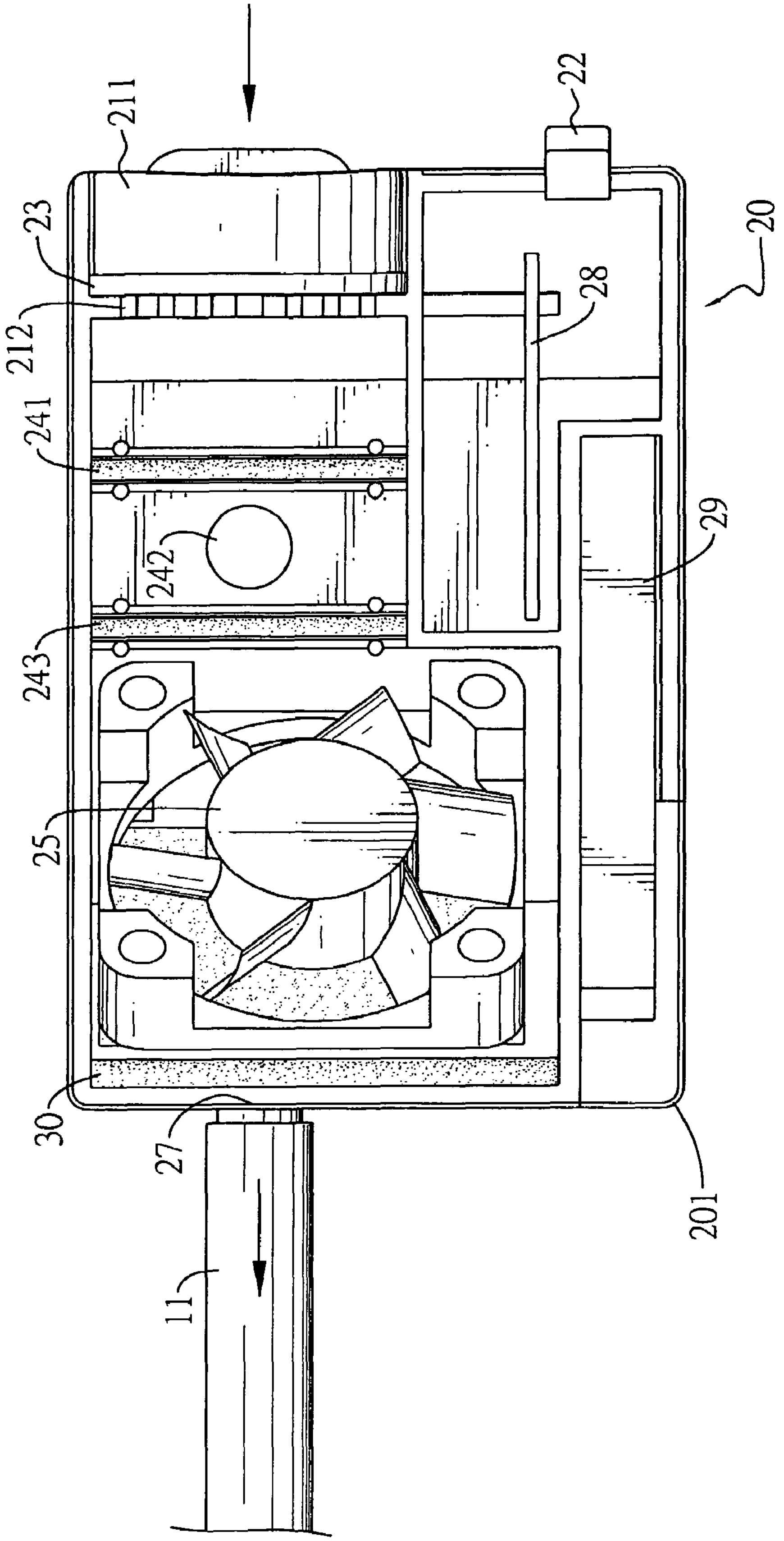
FIG. 4 is a side view of the portable breathing apparatus in accordance with the present invention.

The photocatalyst element (24) comprises two photocatalyst pieces (241, 243) and an ultraviolet light (242) which is mounted between the photocatalyst pieces (241, 243) and is used to sterilize viruses. The photocatalyst pieces (241, 243) can be used with the same shell material as that of the N95 respirator or the P100 respirator. A circuit card (28), which is used to control the filter (20), is provided on a lower end of the shell, and a battery unit (29) as a power supply is mounted in a lower opening end of the shell and can be covered with a battery cap (201). With reference to FIG. 4, after actuating the switch (22), the exhauster (25) begins to rotate thereby inspiriting the external air through the hole (21) so that the external air can be filtered by the multifunctional strainer (23) as a first filtration. Then, the external air passes through the photocatalyst element (24) as a second filtration and a first sterilization. Via the exhauster (25), the external air is mixed with ozone and negative ions, both of which are generated from the high-pressure generator (26), thereby attaining a third filtration and a second sterilization due to the activity of the ozone and the negative ions. Finally, the external air accesses the respirator (10) from the tube (11) through the active carbon net (30) as a fourth filtration.

Hence, the portable breathing apparatus has an excellent effect to filter and sterilize the viruses. Furthermore, the external air flows via the exhauster (25) and therefore, it is easy for the user to breathe. Additionally, materials of the multifunctional strainer (23) and the active carbon net (30) can be replaced after being used for a certain time so that the present invention is safer and more comfortable than the conventional respirator.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A portable breathing apparatus comprising:

a respirator (10) and a filter (20);

the filter (20) having a hollow shell;

a hole (21) defined in a front end of the hollow shell;

a switch (22) provided below the hole (21);

an opening (27) defined in a rear end of the hollow shell;

a tube (11) inserted in the opening (27) and connected to the respirator (10);

a multifunctional strainer (23), a photocatalyst element (24) and an exhauster (25) provided in the hollow shell in turn, and the photocatalyst element (24) having two photocatalyst pieces (241, 243) and an ultraviolet light (242) which is provided between the two photocatalyst pieces (241, 243) for first sterilization;

a circuit card (28) and a battery unit (29) respectively mounted on a lower end of the hollow shell;

the multifunctional strainer (23) mounted adjacent the hole (21) and the exhauster (25) mounted adjacent to the opening (27); and a high-pressure generator (26) and an active carbon net (30) are provided between the opening (27) and the exhauster (25), the high-pressure generator (26) being capable of generating ozone and negative ions for filtration and second sterilization.

2. The portable breathing apparatus as claimed in claim 1, wherein the battery unit (29) is received into a lower opening end of the hollow shell, and the battery unit is covered with a battery cap (201).

3. The portable breathing apparatus as claimed in claim 1, wherein the multifunctional strainer (23) and the active carbon net (30) have replaceable filtering materials.

4. The portable breathing apparatus as claimed in claim 3, wherein a vane cap (211) is inserted in the hole (21), multiple rods (212) are provided adjacent the vane cap (211) and the multifunctional strainer (23) is provided between the vane cap (211) and the multiple rods (212).

5. The portable breathing apparatus as claimed in claim 4, wherein the exhauster (25) is a fan.

6. The portable breathing apparatus as claimed in claim 4, wherein the exhauster (25) is a compressor.

* * * * *